US011399800B2

(12) United States Patent
Sturnick

(10) Patent No.: US 11,399,800 B2
(45) Date of Patent: Aug. 2, 2022

(54) CONSTANT FORCE ULTRASOUND PROBE HANDLE

(71) Applicant: NEW YORK SOCIETY FOR THE RUPTURED AND CRIPPLED MAINTAINING THE HOSPITAL FOR SPECIAL SURGERY, New York, NY (US)

(72) Inventor: Daniel R. Sturnick, New York, NY (US)

(73) Assignee: New York Society for the Relief of the Ruptured and Crippled, maintaining the Hospital for Special Surgery, New York, NY (US)

( * ) Notice: Subject to any disclaimer, the term of this patent is extended or adjusted under 35 U.S.C. 154(b) by 179 days.

(21) Appl. No.: 16/472,006

(22) PCT Filed: Dec. 20, 2017

(86) PCT No.: PCT/US2017/067691
§ 371 (c)(1),
(2) Date: Jun. 20, 2019

(87) PCT Pub. No.: WO2018/119127
PCT Pub. Date: Jun. 28, 2018

(65) Prior Publication Data
US 2020/0015783 A1    Jan. 16, 2020

Related U.S. Application Data

(60) Provisional application No. 62/436,949, filed on Dec. 20, 2016.

(51) Int. Cl.
*A61B 8/00* (2006.01)
*A61B 8/08* (2006.01)

(52) U.S. Cl.
CPC ............ *A61B 8/4455* (2013.01); *A61B 8/429* (2013.01); *A61B 8/4263* (2013.01); *A61B 8/4411* (2013.01); *A61B 8/485* (2013.01)

(58) Field of Classification Search
CPC .................................................... A61B 8/4455
See application file for complete search history.

(56) References Cited

U.S. PATENT DOCUMENTS 4,483,344 A    11/1984  Atkov et al.
4,913,155 A     4/1990  Dow et al.
(Continued)

FOREIGN PATENT DOCUMENTS

CN      203 970 423       12/2014
WO    WO 2012/094308       7/2012

OTHER PUBLICATIONS

Matthew W Gilbertson et al: "Ergonomic control strategies for a handheld force-controlled ultrasound probe", 2012 IEEE/RSJ International Conference on Intelligent Robots and Systems (IROS), Oct. 7, 2012 (Oct. 7, 2012), pp. 1284-1291, XP032287842, DOI: 10.1109/IROS.2012.6385996 ISBN: 978-1-4673-1737-5 *section "III. Mechanical Design" on p. 1285-1286; figures 2-4 *.

(Continued)

*Primary Examiner* — Serkan Akar
*Assistant Examiner* — Aminah Asghar
(74) *Attorney, Agent, or Firm* — Leason Ellis LLP

(57) ABSTRACT

A probe handle accessory for use with a probe includes an outer housing having a first hollow interior and an outer surface for being gripped by a user. The accessory also includes an inner sleeve that is disposed within the first hollow interior and moves axially therein. The inner sleeve having a second hollow interior that is configured to receive the probe and the inner sleeve is configured for securely holding the probe in place within the second hollow interior.

(Continued)

At least one biasing element is provided and is coupled to the outer housing and to the inner sleeve and configured to apply a force to the inner sleeve in a distal direction for maintaining the probe in position against a surface of interest during examination thereof, while permitting axial movement of the inner sleeve within the outer housing.

28 Claims, 12 Drawing Sheets

(56) References Cited

U.S. PATENT DOCUMENTS

| | | | |
|---|---|---|---|
| 4,930,512 A | 6/1990 | Henriksen et al. | |
| 5,116,114 A * | 5/1992 | Nakamura | A61B 3/152 351/205 |
| 5,348,014 A * | 9/1994 | Okado | A61B 5/6843 600/441 |
| 5,842,993 A | 12/1998 | Eichelberger et al. | |
| 5,938,602 A | 8/1999 | Lloyd | |
| 5,938,614 A * | 8/1999 | Sakamoto | A61B 8/4461 600/462 |
| 6,237,192 B1 | 5/2001 | Garrison et al. | |
| 6,261,231 B1 | 7/2001 | Damphousse et al. | |
| 6,434,851 B1 | 8/2002 | Nishina | |
| 2002/0062080 A1 * | 5/2002 | Okawa | A61B 8/4461 600/459 |
| 2002/0062081 A1 * | 5/2002 | Okawa | A61B 8/12 600/459 |
| 2004/0056751 A1 | 3/2004 | Park et al. | |
| 2008/0097408 A1 * | 4/2008 | Murphy | A61B 5/6852 604/533 |
| 2008/0228072 A1 * | 9/2008 | Nycz | A61B 8/0833 600/437 |
| 2009/0071252 A1 | 3/2009 | Van Bekkum et al. | |
| 2009/0306515 A1 * | 12/2009 | Matsumura | A61B 8/4281 600/459 |
| 2010/0049192 A1 * | 2/2010 | Holtz | A61B 18/1492 606/41 |
| 2013/0158410 A1 * | 6/2013 | Ohgishi | A61B 1/00177 600/462 |
| 2013/0167654 A1 | 7/2013 | Ueberschlag et al. | |
| 2013/0194072 A1 * | 8/2013 | Kim | B60B 33/021 340/6.1 |
| 2014/0094701 A1 | 4/2014 | Kwartowitz et al. | |

OTHER PUBLICATIONS

International Search Report and Written Opinion in corresponding International Patent Application No. PCT/US2017/067691 dated Jun. 15, 2018. 13 pages.

* cited by examiner

CONSTANT FORCE ULTRASOUND PROBE HANDLE

CROSS-REFERENCE TO RELATED PATENT APPLICATIONS

This application is based a U.S. National Stage Application under 35 U.S.C. § 371 of International Patent Application No. PCT/US2017/067691, filed Dec. 20, 2017, which claims priority to U.S. Provisional Patent Application No. 62/436,949, filed Dec. 20, 2016, both of which are incorporated by reference herein as if expressly set forth in their respective entireties herein.

TECHNICAL FIELD

The present invention generally relates to medical imaging equipment and more particularly, the present invention relates to a constant force probe handle that is designed to standardize and directly control contact force at the transducer-patient interface as an accessory which is flexible and adaptable for commercially available probes, such as ultrasound probes, and further relates to a probe that incorporates a mechanism for controlling the contact force at the transducer-patient interface.

BACKGROUND

Medical imaging is performed for a wide range of reasons and utilizes a wide range of difference types of equipment. In general, medical imaging is the technique and process of creating visual representations of the interior of a body for clinical analysis and medical intervention, as well as visual representation of the function of some organs and tissues.

One type of medical imaging is ultrasound imaging. As is well known, ultrasound is sound waves with frequencies higher than the upper audible limit of human hearing. Ultrasound is used in many different fields in which there is a desire for imaging and detecting objects and measuring distances. In particular, ultrasound imaging or sonography is often used in medicine; however, other applications include the nondestructive testing or products and structures whereby ultrasound is used to detect invisible flaws and in industrial applications, ultrasound is used for cleaning, mixing, and to accelerate chemical processes.

Within the field of medicine, there are many different ultrasound applications and different acquisition protocols. For example, one specific ultrasound protocol is called shearwave elastography in its application assessing the material properties of musculoskeletal tissues. This is a new application that is rising in popularity throughout the orthopedic field; however, the acquisition of data using this technology is affected by examiner (user) related parameters. Shearwave elastography involves the instigation of a tissue deformation through a focused acoustic radiation force and the simultaneous tracking of resultant strain distribution by the same transducer. Theoretically, the tissue resultant displacement response is directly related to applied magnitude of shearwave force and inversely related to the tissue stiffness. However, one source of artifact includes the tissue deformation induced by the examiner through compression at the transducer-tissue surface interface. While shearwave elastography is a protocol that is uniquely affected by artifact induced by compressive force, quality of all ultrasound acquisition protocols are improved by controlling applied surface contact forces. The present invention is designed to mitigate these artifacts by directly controlling and minimizing the compressive forces induced by the probe on the body surface of subjects examined.

SUMMARY

In one embodiment, the present invention is directed to a constant force probe handle which is designed to standardize and directly control contact force at the transducer-patient interface and can be in the form of an accessory which is flexible and adaptable for most if not all commercial available medical imaging probes, such as an ultrasound probe. As a result of the present invention, minimized and controlled deformation from compressive forces will result in enhanced ultrasound image acquisition in practice with reduced artifact in shearwave elastography measurements. Additionally, the features of the present device provide similar benefits and value to a wide range of instrument transducer in a variety of other applications beyond ultrasound applications.

In another embodiment, a method of acquiring images while imposing direct constraint of a contact force between a handheld probe and a subject body comprises the steps of: (1) coupling the probe to a handle body that includes an outer housing and an inner sleeve that is axially moveable within the outer housing, the probe being carried by the inner sleeve; (2) applying a constant and at least substantially fixed magnitude of force to the probe in a direction toward the subject body; and (3) maintaining the constant and the at least substantially fixed magnitude of force over a range of axial displacement of the probe within the handle body.

In another aspect, a probe system is provided and is configured for placement against and movement along a body of interest and is configured to control and minimize compressive forces induced by a probe on the body of interest. The probe has a head portion that is intended for placement against the surface of interest. The probe system also includes a probe handle accessory for holding the probe. The probe handle accessory includes an outer housing having a first hollow interior and an outer surface for being gripped by a user. The accessory further includes an inner sleeve that is disposed within the first hollow interior and moves axially therein. The inner sleeve has a second hollow interior that receives the probe with the probe being fixedly held in place within the second hollow interior. At least one biasing element is coupled to the outer housing and to the inner sleeve and configured to apply a force to the inner sleeve and to the probe in a distal direction for maintaining the probe in position against the surface of interest during examination thereof, while permitting axial movement of the inner sleeve and probe within the outer housing due to counter forces being applied to the probe.

BRIEF DESCRIPTION OF THE DRAWING FIGURES

DETAILED DESCRIPTION OF CERTAIN EMBODIMENTS

As used herein, the term "constant force" in the context of a probe handle, such an ultrasound probe handle, and alternatively, a modified probe, such as an ultrasound probe, of the present invention refers to the fact that the probe handle constrains the force applied by the transducer head to an at least substantially fixed value (magnitude), allowing for displacement of the probe handle through mediation with the constant force biasing mechanism disclosed herein.

Figure 1:
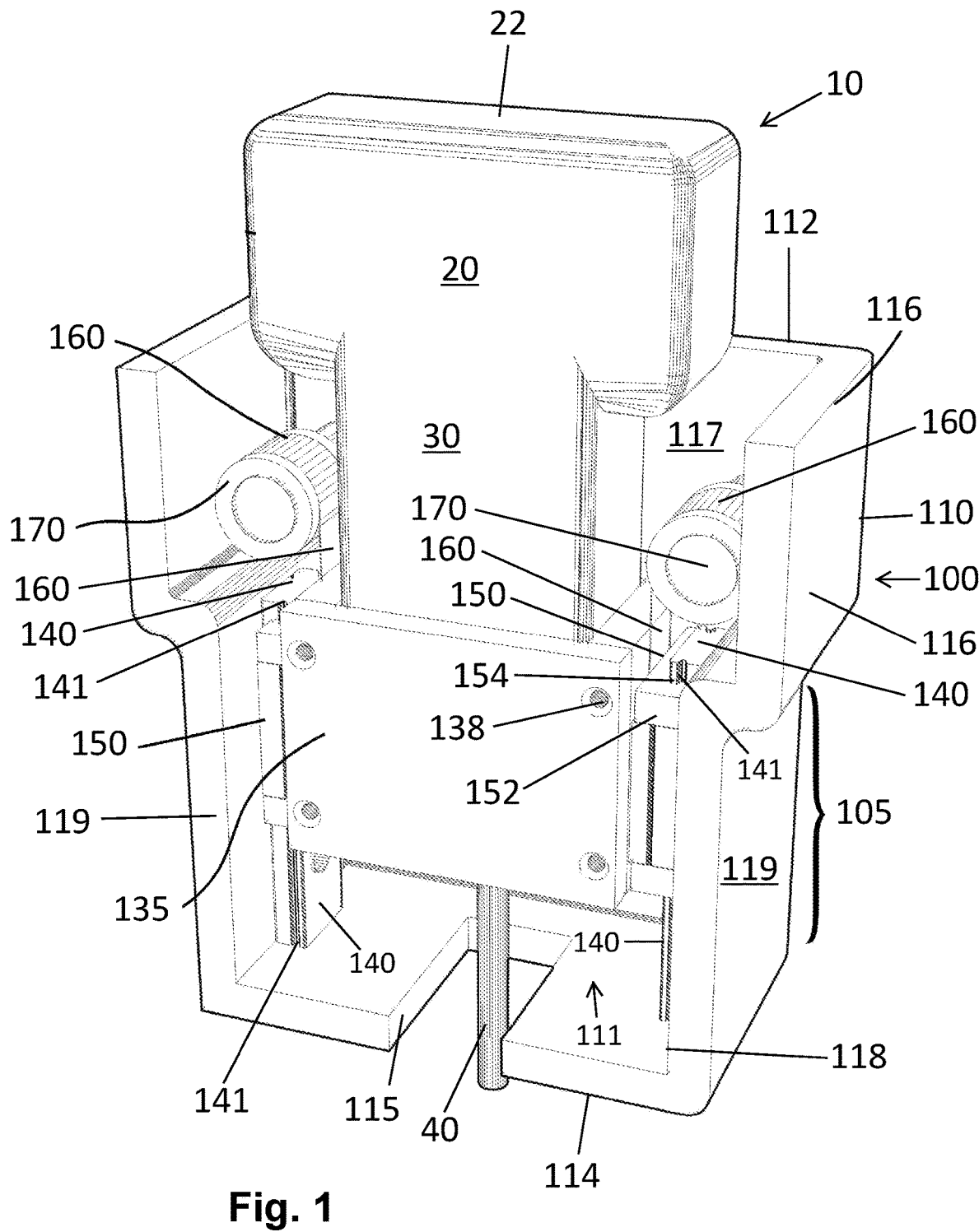
FIG. 1 is a front and side perspective view of a constant force ultrasound probe handle in accordance with a first embodiment.
Figure 2:
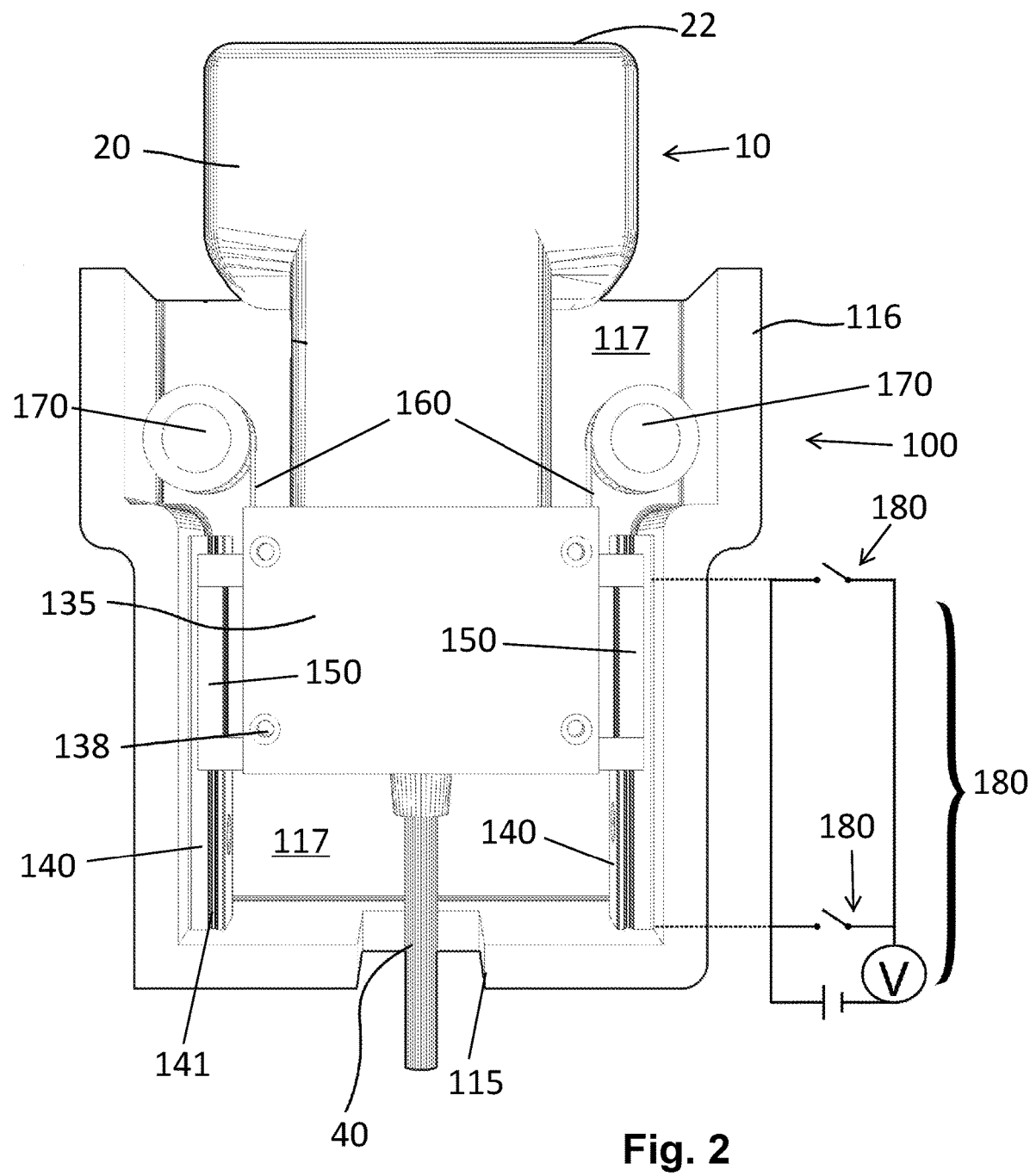
FIG. 2 is a front perspective view thereof.

FIGS. 1 and 2 illustrate a constant force ultrasound probe handle 100 in accordance with a first embodiment of the present invention and being configured for use with a probe, such as an ultrasound transducer probe 10. As is known, an ultrasound transducer probe is typically in the form of a wand-like instrument that gives off sound waves and picks up the echoes as they bounce off the organs. It is a device, usually electrical, or, in some cases, mechanical, that converts one type of energy to another. The transducer, or probe, 10 is the main part of an ultrasound machine. The transducer (probe) 10 sends ultrasound waves into the body and receives the echoes produced by the waves when it is placed on or over the body part being imaged.

For purpose of illustration, the ultrasound transducer probe 10 has a probe body that is defined by a distal transducer head 20 and a proximal base 30. The ultrasound transducer probe 10 is powered and typically, has a probe cord 40 that is coupled to and extends outwardly from the proximal base 30 (e.g., extends from a proximal end of the proximal base 30). The probe cord 40 can be connected to a console (not shown) of the ultrasound machine. The illustrated ultrasound transducer probe 10 is T-shaped with the distal transducer head 20 being enlarged relative to the proximal base 30 (it will be understood that the simplified representation of the ultrasound probe is characteristically typical in medical applications, probe shapes and sizes vary across different manufacturers and applications; however, as discussed herein, the present invention is amendable to use with most if not all ultrasound probe designs). The distal transducer head 20 has an exposed distal surface 22 that is intended for placement on the body of interest, such as the patient's tissue (e.g., skin). The distal surface 22 can be an at least substantially flat surface or can be slightly curved.

As described herein, the constant force ultrasound probe handle 100 is configured to mate with and be coupled to the ultrasound transducer probe 10 as an accessory, and together the two form a single integrated structure (unit). The constant force ultrasound probe handle 100 includes an external (outer) housing or outer casing 110 that is shaped and sized to receive the ultrasound transducer probe 10. The casing 110 defines a hollow interior 111. The casing 110 has an open first end 112 and a partially open second end 114. As illustrated, the casing 110 can have an enlarged portion 116 at the open first end 112 (i.e., the distal end) to accommodate the enlarged distal transducer head 20 and have a narrower proximal portion 118. The partially open second end 114 has an opening 115 that receives and allows the probe cord 40 to pass through from the hollow interior 111 to the outside of the ultrasound transducer probe 10. The casing 110 can generally have a square or rectangular shape defined by a pair of side walls, a front wall, and a rear wall. It will be appreciated that one of the walls of the casing 110 can be opened or moved to allow access to the hollow interior. For example, one of the walls can be pivotally (e.g., hingedly connected) to the other walls of the outer casing 110 and thus movable between an open position and a closed position. As shown in FIGS. 1 and 2, the proximal portion 118 includes a pair of opposing side walls 119 and a rear wall 117 that extends to and forms part of the enlarged portion 116. The side walls 119 are parallel to one another and are perpendicular to the front wall and the rear wall.

Figure 3:
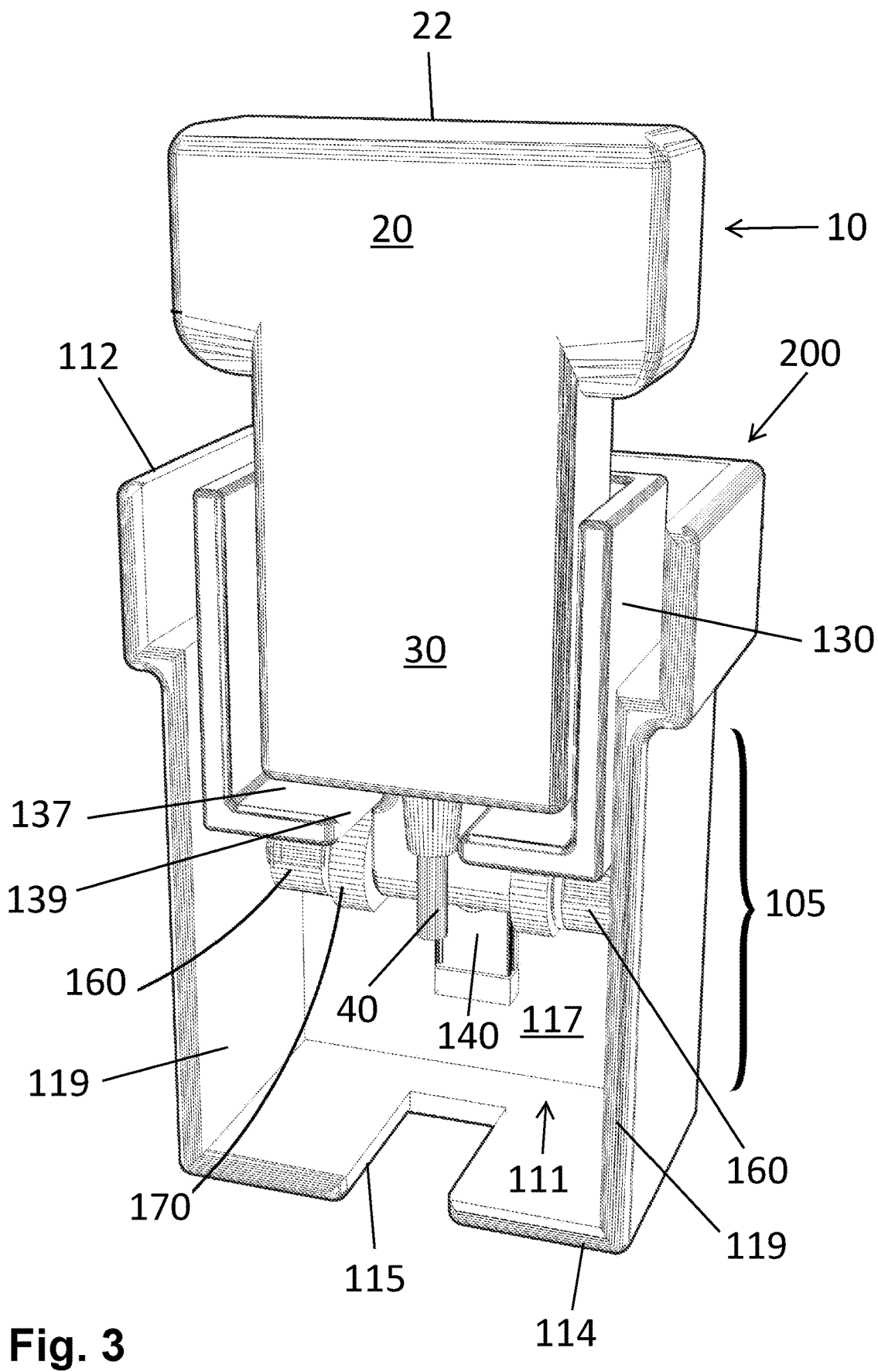
FIG. 3 is a front and side perspective view of a constant force ultrasound probe handle in accordance with a second embodiment and shown in a first position.
Figure 4:
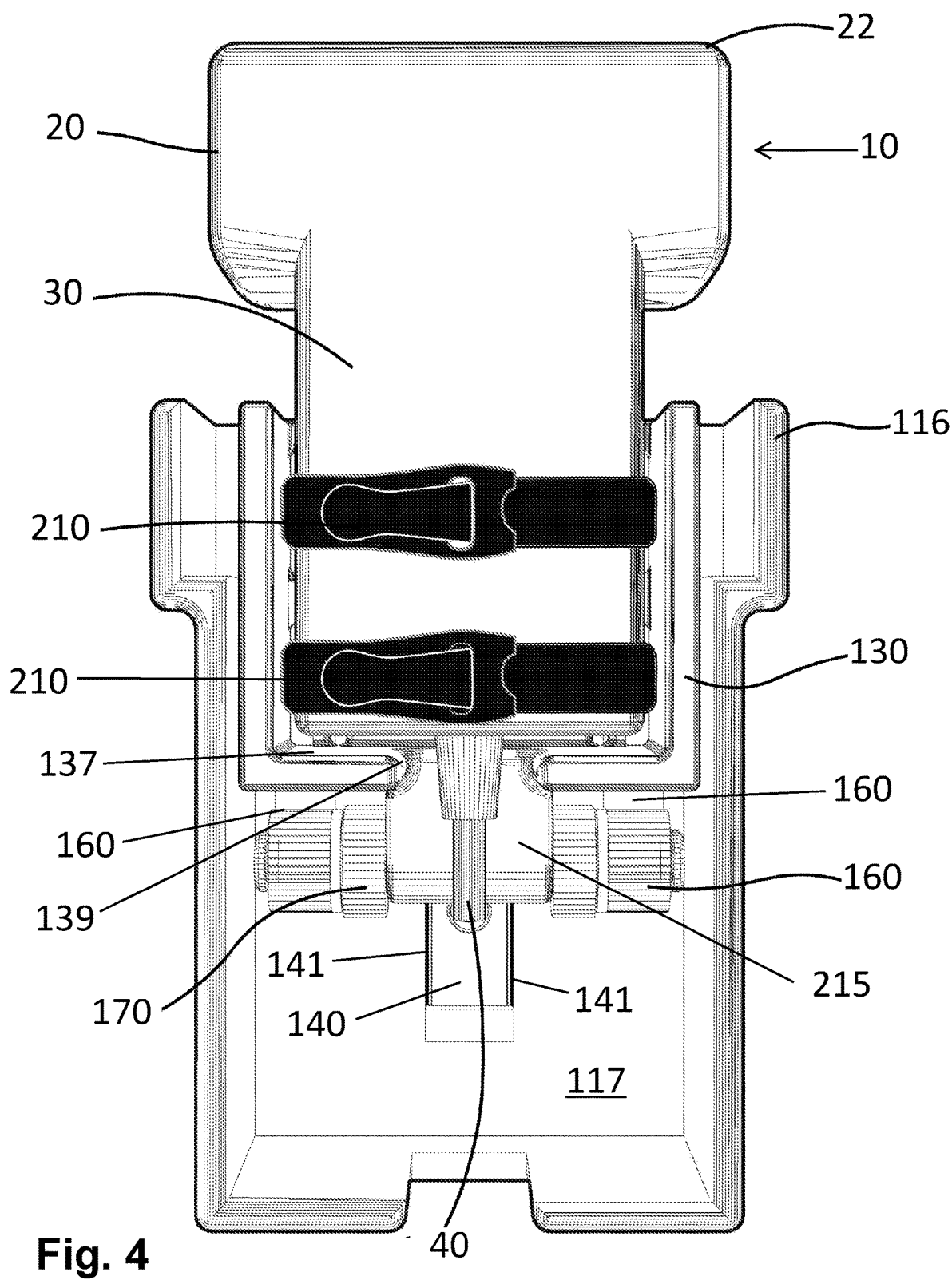
FIG. 4 is a front perspective view thereof.
Figure 5:
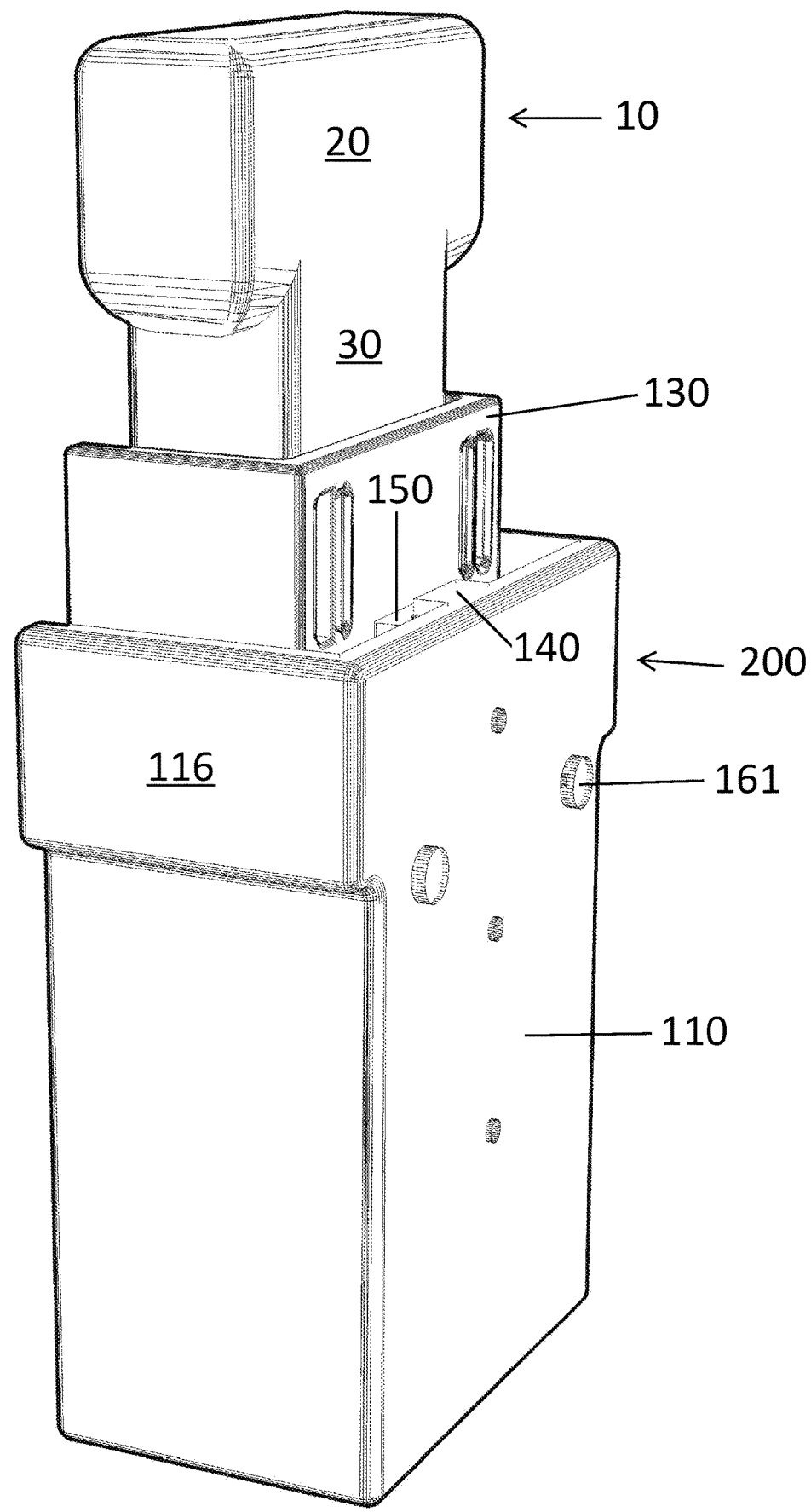
FIG. 5 is a side and rear perspective view of the constant force ultrasound probe handle of FIG. 3.
Figure 6:
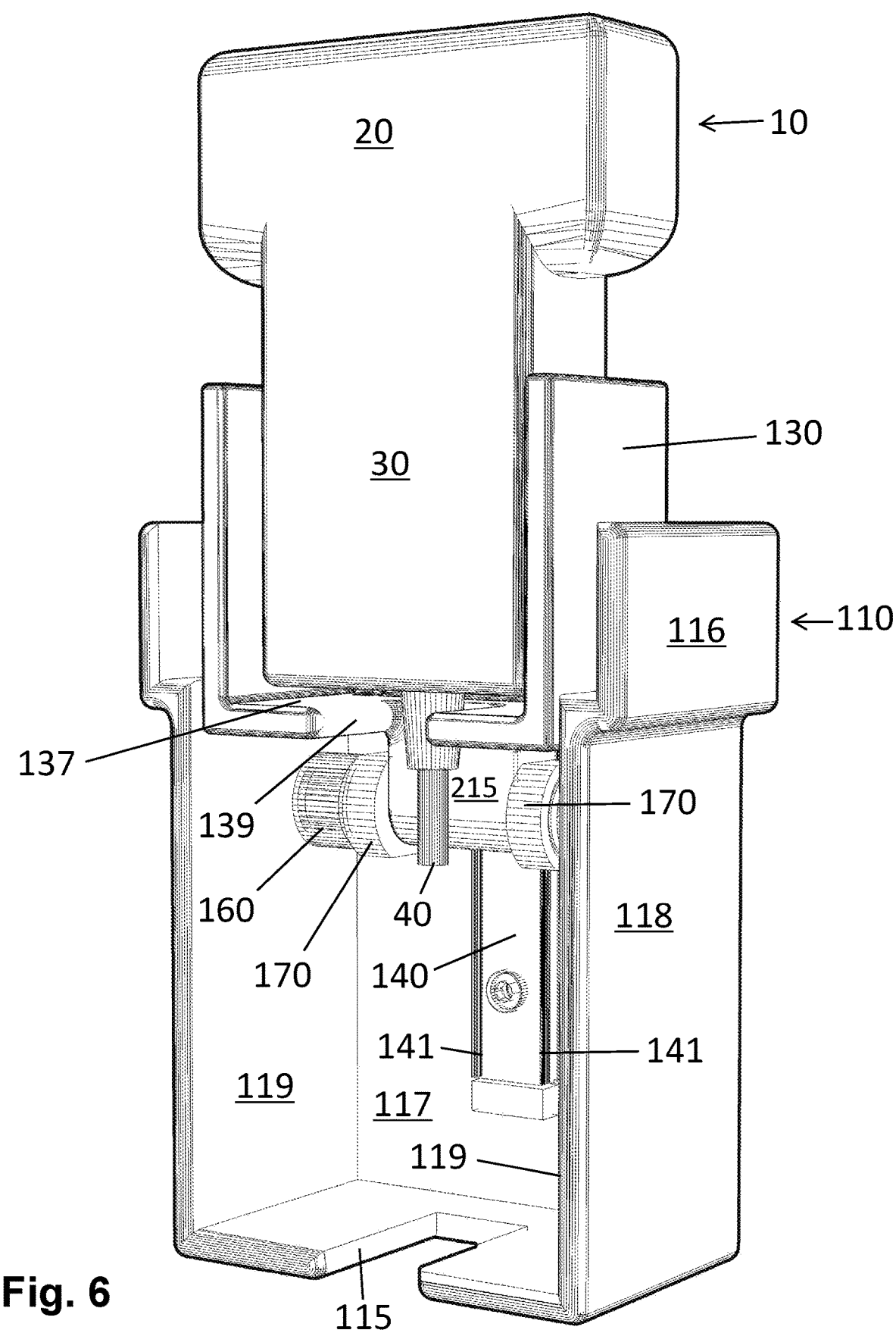
FIG. 6 is a front and side perspective view of the constant force ultrasound probe handle of FIG. 3 being shown in a second position.
Figure 7:
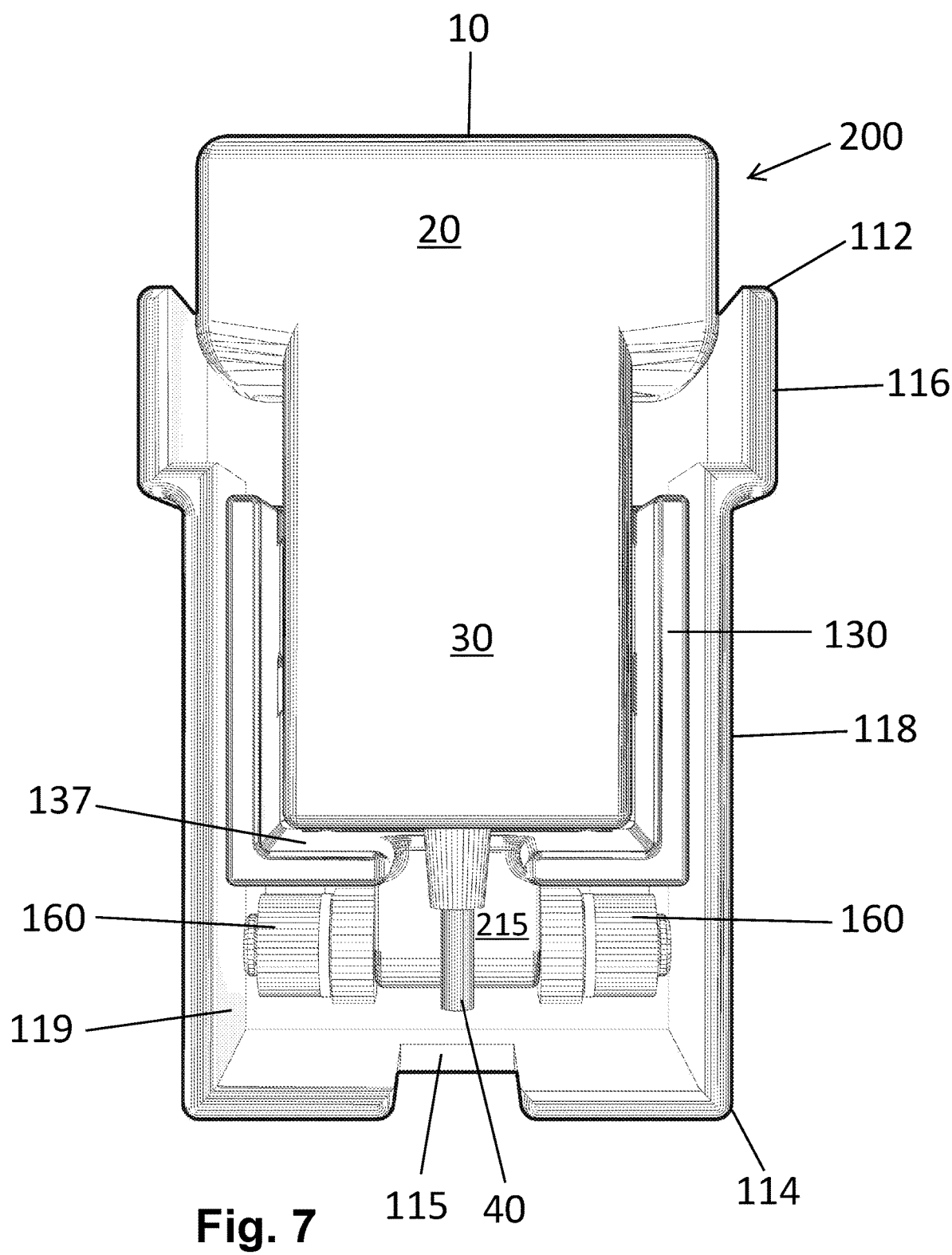
FIG. 7 is a front perspective view of the constant force ultrasound probe handle of FIG. 3 being shown in a third position.
Figure 8:
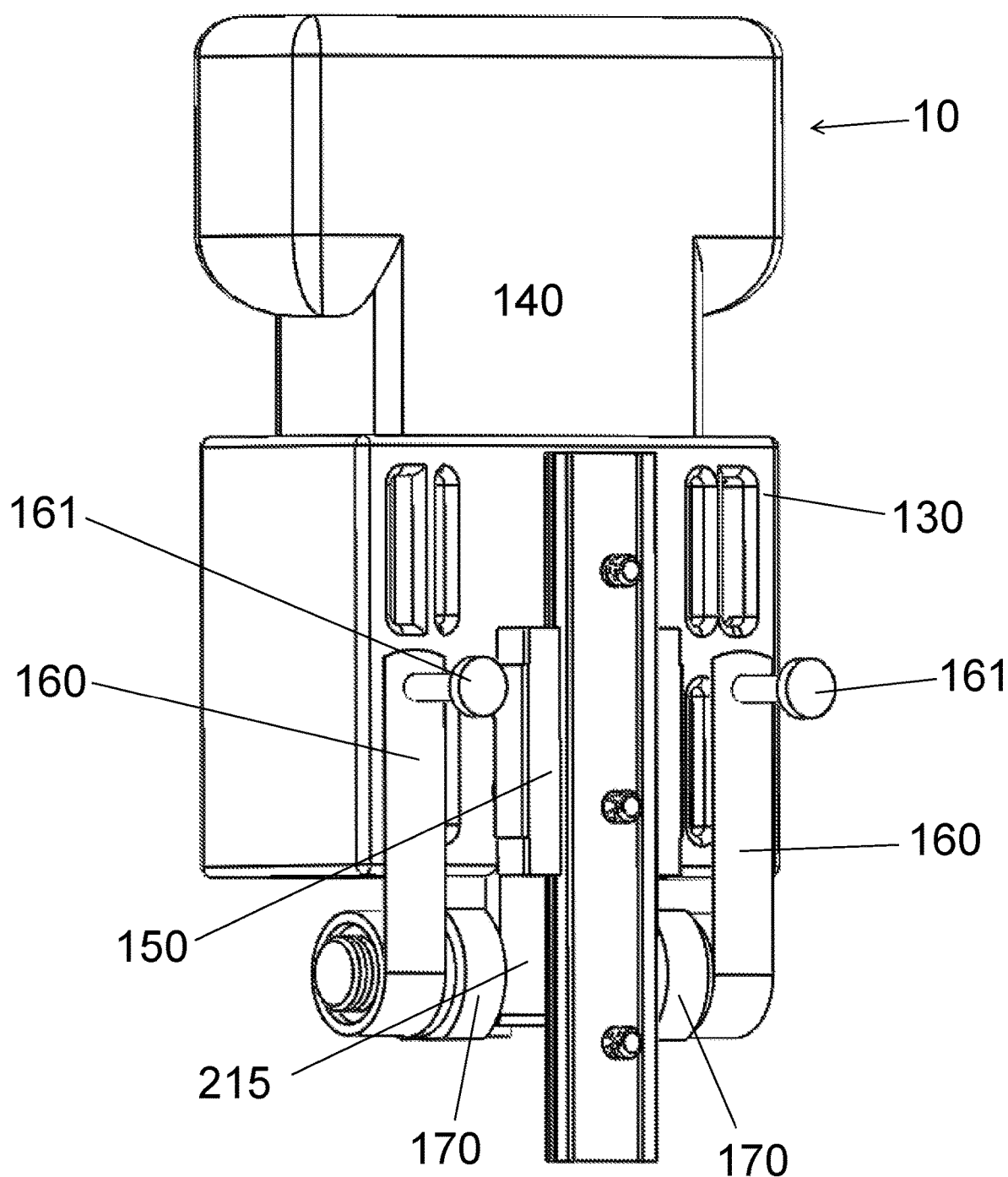
FIG. 8 is a rear and side perspective view with an outer casing being removed to illustrate a guide rail and an inner sleeve along with biasing elements.

The constant force ultrasound probe handle 100 also includes an inner sleeve or inner housing (casing) 130 that is configured to receive, hold, and carry the proximal base 30. The inner sleeve 130 is fixedly yet detachably coupled to the probe 10 such that motion of the inner sleeve 130 is translated into motion of the probe 10. The inner sleeve 130 thus has a complementary shape and size relative to the probe 10 and more particularly, the proximal base 30 thereof. In the illustrated embodiment, the inner sleeve 130 has a square or rectangular shape. It will also be appreciated that there are a number of different techniques for detachably coupling the proximal base 30 to the inner sleeve 130. For example and as shown, in one embodiment, inner sleeve 130 is a three-sided structure with a fourth side being defined by a removable side wall or plate 135 that serves to encapsulate and surround at least a section of the probe base 30. The inner sleeve 130 also has a floor 137 (FIGS. 3 and 4) that has an opening or slot 139 (FIGS. 3 and 4) through which the probe cord 40 passes. The proximal base 30 of the probe 10 can seat against the floor 137 and the probe cord 40 can be inserted into the slot 139 since the slot 139 is open along one side or edge (e.g., front edge) of the floor 137.

Removal of the plate 135 creates an opening or space through which the proximal base 30 can be inserted into a hollow interior of the inner sleeve 130. The proximal base 30 can be inserted into the hollow interior of the inner sleeve 130 and then the plate 135 can be attached to the three-sided body of the inner sleeve 130, thereby encapsulating the proximal base 30. The attachment of the plate 135 to the remaining three-sided body of the proximal base 30 results in the proximal base 30 being securely held within the inner sleeve 130 such that the two elements move as a single structure. The plate 135 can be attached to the three-sided body of the inner sleeve 130 using traditional techniques, such as the use of fasteners 138, such as screws, bolts, or other types of quick connectors, etc.

The inner sleeve 130 is mounted on at least one guide rail 140 to guide linear movement of the inner sleeve 130, and the carried probe 10, within the outer casing 110. The guide rail 140 can be in the form of a ball-bearing guide rail. In the illustrated embodiment, there are a pair of guide rails 140 that are disposed opposite one another and in particular, the guide rails 140 are disposed along the pair of opposing side walls 119 of the proximal portion 118 of the outer casing 110. Each guide rail 140 can be in the form of a linear rail that can have a recessed track 141 formed along one or more of its exposed edges. In the illustrated embodiment, the two side edges have recessed tracks 141. The guide rails 140 extend along the side wall 119 but do not extend into the enlarged portion 116.

The inner sleeve 130 mates with the guide rails 140 by means of a pair of coupling members (connectors) 150 that are located along two end walls 133 of the inner sleeve 130. Each coupling member 150 can be in the form of a C-shaped structure that receives the guide rail 140 and mates therewith. In particular, the two ends walls 152 of the coupling member 150 can include a longitudinal protrusion (or rail) 154 that is received within one of the recessed tracks 141. The mating/coupling between the coupling members 150 and the guide rails 140 prevents unwanted lateral movement of the inner sleeve 130 but allows for linear (longitudinal) movement of the inner sleeve 130 within the outer casing 110. The coupling between the inner sleeve 130 and the outer casing 110 is thus a male/female connection. In this way, the inner sleeve 130 can ride up and down the guide rails 140 (linear motion) based on forces being applied to the probe 10 which is translated to the inner sleeve 130 and for controlling the applied contact forces.

The constant force ultrasound probe handle 100 also includes a biasing element(s) that serves to apply and maintain a force on the inner sleeve 130 and thus to the probe 10 that is contained therein. More specifically, the biasing elements can be in the form of a pair of constant force springs 160 that are coupled to the inner sleeve 130. As is known, the constant force spring 160 is a spring for which the force it exerts over its range of motion is a constant or at least substantially constant. Generally constant force springs are constructed as a rolled ribbon of spring steel such that the spring is relaxed when it is fully rolled up. As it is unrolled, the restoring force comes primarily from the portion of the ribbon near the roll. Because the geometry of that region remains nearly constant as the spring 160 unrolls, the resulting force is nearly constant. While the constant force spring 160 can be in the form of a stainless-steel spring, it will be understood that the constant force spring 160 can be formed of other suitable materials and/or can take different forms. For example, the constant force spring 160 can be formed of a shape memory alloy, such as nitinol, and be configured to apply a constant force as described herein.

One of the constant force springs 160 is disposed near one side wall of the enlarged portion 116, while the other constant force springs 160 is disposed near the opposite side wall of the enlarged portion 116. One end of one constant force spring 160 is attached to the inner sleeve 130 (i.e., attached to an end wall of the inner sleeve 130).

As shown, the constant force ultrasound probe handle 100 includes a pair of pulleys 170 that are fixedly attached to the rear wall 117. One pulley 170 is located on one side of the probe 10 and the inner sleeve 130 and the other pulley 170 is located on the other side of the probe 10 and the inner sleeve 130. Each pulley 170 is located within the enlarged portion 116 above the area where the side wall (end wall) of the outer casing 110 flares radially outward to form the enlarged portion 116. The pulley 170 is thus mounted to a shaft that is rotatably coupled to the rear wall 117. Each constant force spring 160 is wound about one respective pulley 170 or structure coupled thereto and extends to the inner sleeve 130 to apply an at least substantially constant force to the inner sleeve 130.

The enlarged portion 116 of the outer casing 110 also defines a grip portion 105 that represents the portion of the outer casing 110 below the shoulder representing the interface between the enlarged distal portion 116 and the narrower proximal portion 118. This grip portion 105 is the area that is intended to be grasped and gripped by the user during use of the probe 10 as during an ultrasound imaging procedure.

The constant force ultrasound probe handle 100 can also further include sensors or detectors 180 that monitor the degree of travel of the inner sleeve 130 within outer casing 110. More specifically and according to one embodiment, the sensors/detectors 180 comprise two pairs of sensors 180. Within each pair of sensors 180 is an upper (first) sensor 180 and a lower (second) sensor 180. The upper sensors 180 are located at or proximate to first (upper) ends of the carriage rails 140, while the lower sensors 180 are located at or proximate to second (lower) ends of the carriage rails 140. The upper sensors 180 thus detect when the inner sleeve 130 reaches the first ends of the two carriage rails 140, and similarly, the lower sensors 180 detect when the inner sleeve 130 reaches the second ends of the two carriage rails 140. In one embodiment, the sensors 180 are in the form of switches, such as electrical contact switches which monitor for the inner sleeve 130 extending into contact with either end of the bearing carriage rail 140 travel length.

The constant force probe handle 100 is interfaced to the base 30 of the probe 10 directly below the transducer head 20, with its cord 40 extending through the slot 115 of the outer casing 110. The probe base 30 is placed within the inner sleeve 130, secured by the interior sleeve top plate 135, and allows the inner sleeve 135 of the handle 100 to freely slide along the ball-bearing carriage rail 140. The user then grasps the grip portion 105 of the outer casing 110 to perform image acquisition. The user can engage the transducer end (transducer head 20) of the probe 10, while the inner sleeve 130 slides along the bearing rail 140, while the constant force springs 160 extended from bearings rails or pulleys 170 ensure a minimal and constant compression force between the transducer end (head) 20 and the body surface of the subject being examined. The contact switches 180 close a circuit when the inner sleeve 130 is in contact with either end of the ball-bearing carriage rail 140. This mechanism can be used to indicate to the user or can be interfaced with ultrasound system to restrict image acquisition when transducer compressive force is outside of constant force control.

It will be appreciated that the width of the ultrasound probe head 20 is selected such that it can be received within the enlarged portion of the outer casing 110. In other words, if a force is applied to the probe head 20 in a direction toward the interior of the handle 100, the probe head 20 is pushed inside of (it retracts) of the outer casing 110. In a rest position, the probe head 20 extends beyond the distal end of the outer casing 110.

FIGS. 3-12 illustrate a constant force ultrasound probe handle 200 in accordance with a second embodiment of the present invention and configured for use with the ultrasound transducer probe 10. The constant force ultrasound probe handle 200 is very similar to the constant force ultrasound probe handle 100 and therefore, like elements are numbered alike.

One difference is that the inner sleeve 130 of the handle 200 does not include the plate 135 for securely holding the probe 10 in place within the inner sleeve 130. Instead, the inner sleeve 130 includes one or more fasteners 210 that serve to hold the probe 10 in place. For example, the fasteners 210 can be in the form of a pair of straps that are spaced apart from one another and each includes a means for attaching one end of the strap to the other end of the strap. For example, each strap can include hook and loop material (patches) at the two ends of the strap to allow the strap to be routed arounds the probe 10 and then attached to one another, thereby resulting in the probe 10 being captured and held by each strap. Alternatively, the straps can include buckles or the like or other mechanisms to allow attachment of the two ends of the straps. Each strap 210 can be attached to the rear wall 117 resulting in the two ends of the strap 210 being free.

The straps 210 thus provide an easy yet effective means for releasably holding the probe 10 in place within the inner sleeve 130. As mentioned herein, the plate 135 is eliminated in this embodiment.

The handle 200 also includes an alternative manner for mounting the at least one guide rail 140 and the pulleys 170. More specifically, the at least one guide rail 140 comprises a single guide rail 140 that is fixedly disposed (in a longitudinal direction) along the rear wall 117. The guide rail 140 can be the same or identical to the one used in the handle 100 with the exception that the size of the guide rail 140 can be increased when only one is used along the rear wall 117. As shown, each side edge of the guide rail 140 can includes a recessed track (longitudinal grove) 141 that faces outward away from the rear wall 117. As in the previous embodiment, the guide rail 140 defines the length of travel of the inner sleeve 130 and thus, of the probe 10 that is held and carried by the inner sleeve 130.

The inner sleeve 130 mates with the guide rail 140 by means of a single coupling member 150 that is disposed along the rear surface of the inner sleeve 130. The coupling member 150 can be in the form of a C-shaped structure (block) that receives the guide rail 140 and mates therewith. In particular, each of the two end walls 152 of the coupling member 150 includes a longitudinal protrusion (or rail) 154 that is received within one of the recessed tracks 141. The longitudinal rails 154 thus face one another with an open space 157 formed therebetween. The mating/coupling between the coupling member 150 and the guide rail 140 prevents unwanted lateral movement of the inner sleeve 130 but allows for linear (longitudinal) movement of the inner sleeve 130 within the outer casing 110. The coupling between the inner sleeve 130 and the outer casing 110 is thus a male/female connection in which the guide rail 140 is slidingly received within the space 157 with the rails 154 (male protrusion) being slidingly received within the recessed tracks 141. In this way, the inner sleeve 130 can ride up and down the guide rail 140 based on forces being applied to the probe 10 which is translated to the inner sleeve 130. The length of the guide rail 140 defines the degree of travel of the inner sleeve 130 and probe 10.

As mentioned, the arrangement of the pulleys 170 and the constant force springs 160 also differs in the handle 200 compared to the handle 100. In particular, the inner sleeve 130 has a downwardly extending protrusion that is centrally located and extends below the bottom surface of the floor 137 of the inner sleeve 130. The protrusion can be thought of as being a pulley housing or lower housing 215 as described herein. As illustrated, both the slot 139 and the lower housing 215 are centrally located with the lower housing 215 being located rearward to the slot 139 such that the probe cord 40 is located in front of the lower housing 215 as illustrated. The lower housing 215 is a hollow structure that is intended and configured to support the pulleys 170 and related hardware, such as rotatable axles/shafts, etc. As illustrated, there are two pulleys 170 one on either side of the lower housing 215.

Figure 9:
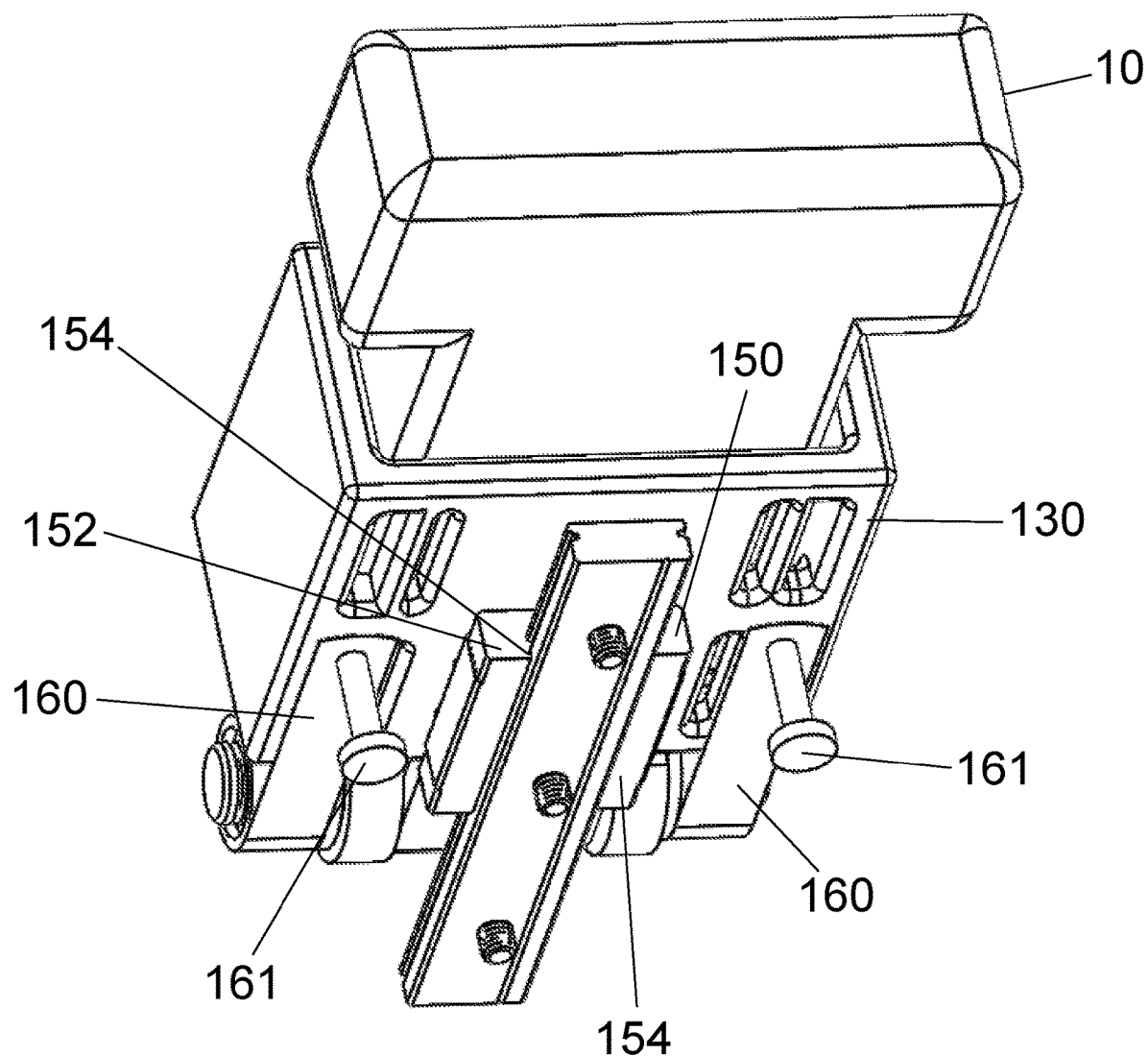
FIG. 9 is a top and rear perspective view with the outer casing and guide track being removed to illustrate a coupling member disposed along a rear of the inner sleeve.
Figure 10:
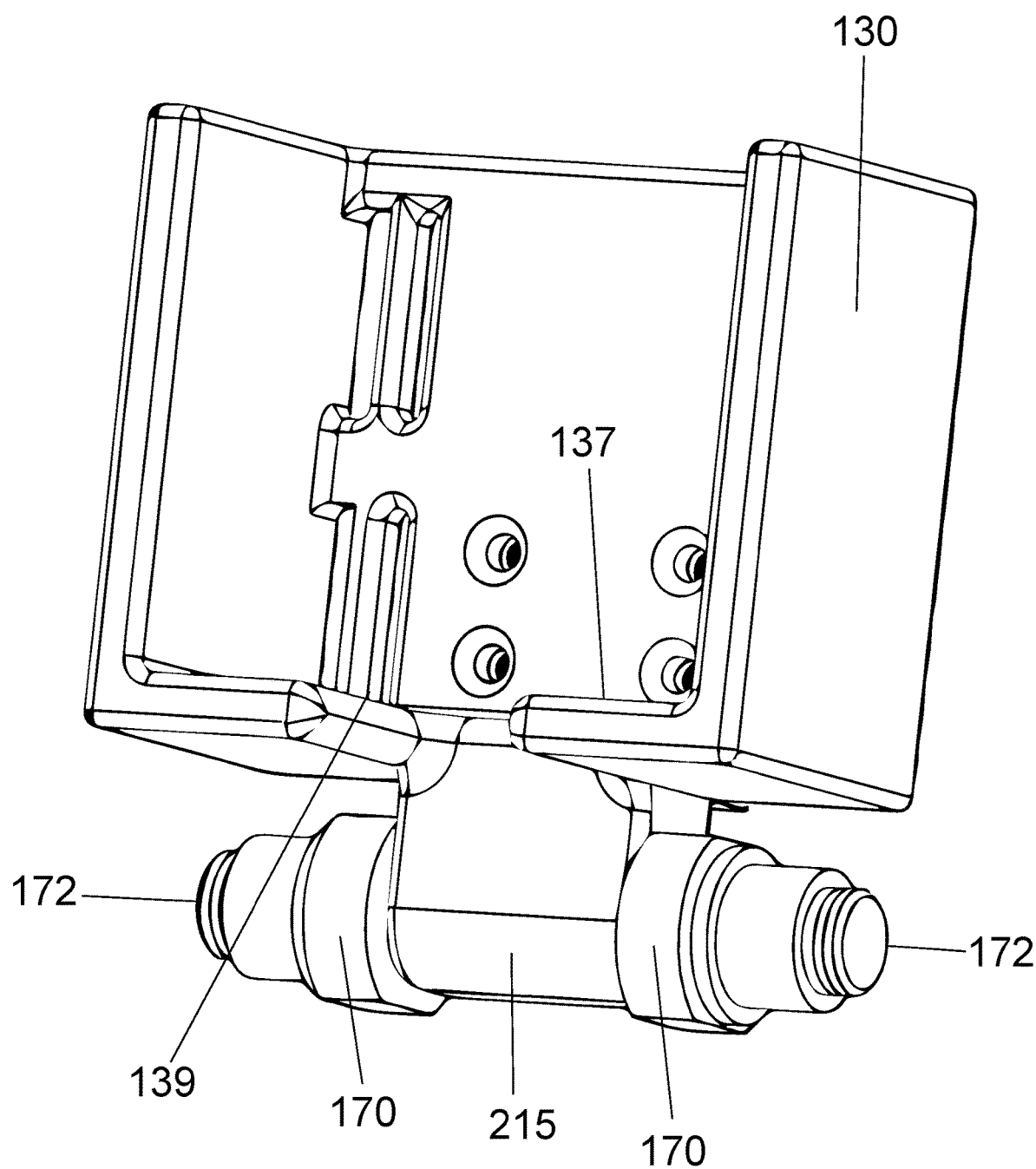
FIG. 10 is a front and bottom perspective view of the inner sleeve with an integral pulley assembly.
Figure 11:
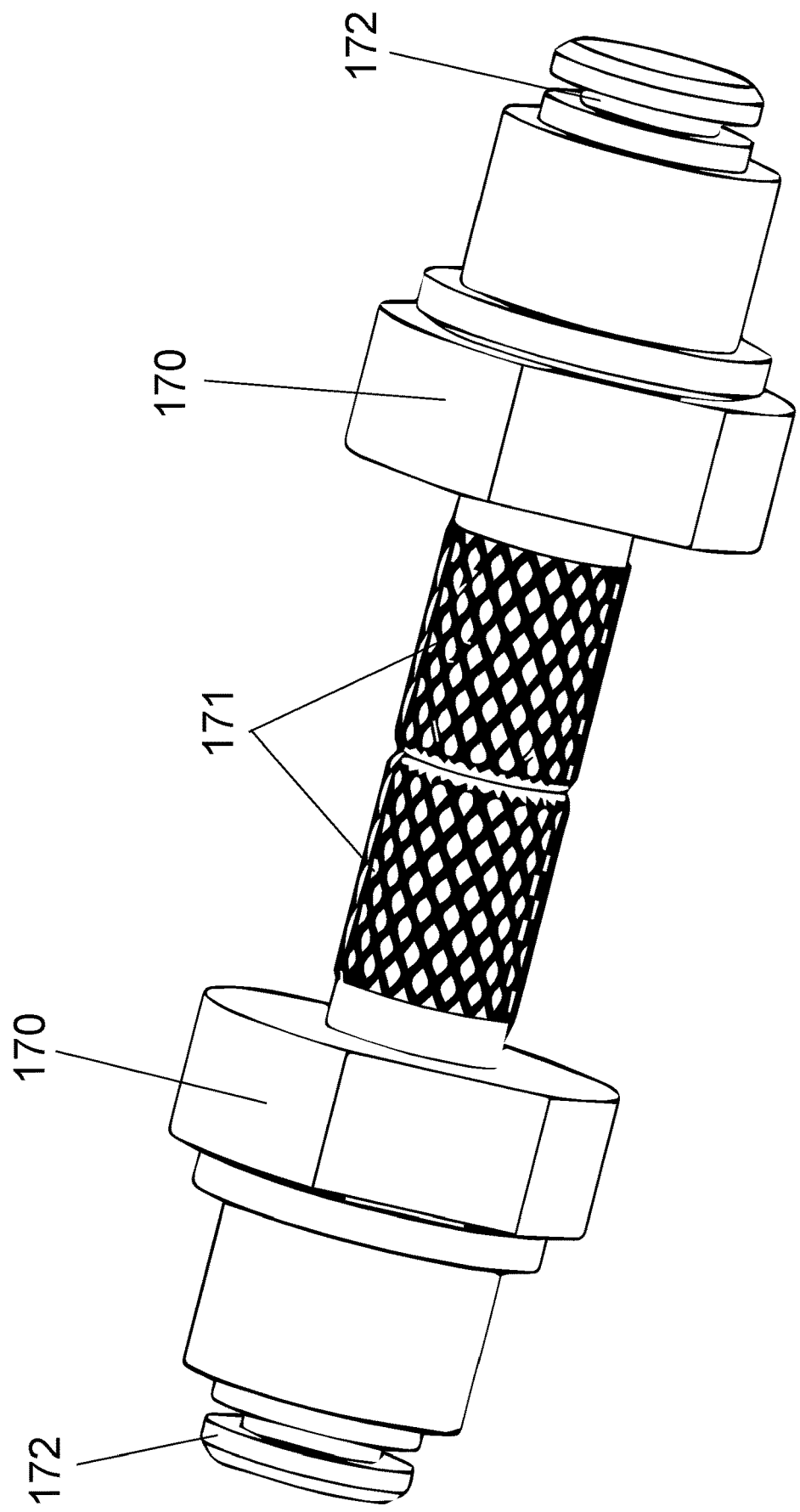
FIG. 11 is a perspective view of the pulley assembly.

As shown in FIGS. 9-11, each pulley 170 can have an inner shaft portion 171 that is disposed within the lower housing 215 and an outer shaft portion 172 that is disposed outside of the lower housing 215. The pulley 170 has an annular shaped body 175 centrally disposed between the inner shaft portion 171 and the outer shaft portion 172. The inner shaft portions 171 can be coupled to one another such that the pulleys 170 rotate in unison. Alternatively, each pulley 170 can have its own associated inner shaft portion 171 that is rotatable mounted in the lower housing 215.

About the outer shaft portion 172 a coil can be provided and is configured such that the constant force spring 160 can be wound about and fixedly attached to the coil. As will be appreciated, the coil is fixedly attached to the outer shaft portion 172 such that the two rotate in unison as when the constant force spring 160 is either being wound about the coil due to linear movement of the inner sleeve 130 in a first direction or being unwound (uncoiled) from the coil due to linear movement of the inner sleeve 130 in an opposite second direction.

In contrast to the first embodiment, one free end of the constant force spring 160 that is opposite the coiled portion is fixedly attached to the outer casing 110 and more particularly, to the rear wall 117 of the outer casing 110. For example, a fastener 161 or the like, such as a rivet, pin, bolt, hook, etc., can be used to fixedly attach the one free end of the constant force spring 160 to the rear wall 117 of the outer casing 110. Since the other end of the constant force spring 160 is wound about a part (i.e., the pulley assembly) that is carried by the inner sleeve 130, in a rest position, the constant force spring 160 will pull (apply a force to) the inner sleeve 130 to a rest position. As shown, the rest position is one in which the probe head 20 extends beyond the distal end (enlarged portion) of the outer casing 110. As described herein, when a force is applied to the probe head 20, as when the probe head 20 is placed against tissue during an imaging procedure, the probe 10 and the inner sleeve 130 retract within the outer casing 110 and the constant force spring 160 stores energy and applies a counter force. The operation of the handle 200 is described below.

It will be appreciated that while the handle 100, 200, as well as other handles described herein, are discussed in terms of being used with the ultrasound transducer probe 10, it within the scope of the present invention that the handles disclosed herein can be used with other probes. Accordingly, the discussion of the handle 100, 200 being used in ultrasound applications is merely exemplary of the present invention and not limiting. Further, as discussed herein, the features of the handle 100, 200 can be directly incorporated into the ultrasound transducer probe 10 itself. In other words, the teachings of the present invention can be implemented as an accessory that can be used with and coupled to the ultrasound transducer probe 10 or it can be directly incorporated into the construction of the ultrasound transducer probe 10 as described below.

As discussed herein, the basic components of contemporary ultrasound transducers include the impedance head 20, a piezoelectric element, the cord 40 for alternating current power supply, and insulation material for vibration reduction, all within an exterior housing of the probe 10. The constant force method could be applied within the probe housing itself, similarly allowing the impedance head 40, piezoelectric element, and insulation material to translate while interfaced with a constant force spring 160 to constrain the magnitude of force (F) applied by the probe head 20.

Like handle 100, the constant force ultrasound probe handle 200 can also further include sensors or detectors 180 that monitor the degree of travel of the inner sleeve 130 within outer casing 110. More specifically and according to one embodiment, the sensors/detectors 180 comprise at least one pair of sensors 180. The pair of sensors 180 comprises an upper (first) sensor 180 and a lower (second) sensor 180. The upper sensor 180 is located at or proximate to first (upper) ends of the carriage (guide) rail 140, while the lower sensor 180 is located at or proximate to second (lower) ends of the carriage (guide) rail 140. The upper sensor 180 thus detects when the inner sleeve 130 reaches the first ends of the carriage (guide) rail 140, and similarly, the lower sensor 180 detects when the inner sleeve 130 reaches the second end of the carriage rail 140. In one embodiment, the sensors 180 are in the form of switches, such as electrical contact switches which monitor for the inner sleeve 130 extending into contact with either end of the bearing carriage (guide) rail 140 travel length.

Use of the Handle (Accessory) 100, 200

The constant force probe handle 200 is interfaced to the base handle 30 of the probe 10 directly below the transducer end (head) 20, with its cord 40 extending through the handle 200. The probe base 30 is placed within the interior sleeve 130, secured by the interior sleeve top plate 135 or straps 210, and allows the interior sleeve 130 of the handle to freely slide along the ball-bearing carriage (guide) rail 140. The user then grasps the grip 105 of the outer casing 110 to perform image acquisition. The user can engage the transducer end 20 of the probe 10, while the inner sleeve 130 slides along the bearing guide rail 140 while the constant force springs 160 extended from bearings rails or pulleys 170 ensure a minimal and constant compression force between the transducer end 20 and the body surface of the subject being examined. The contact switches 180 close a circuit when the inner sleeve 130 is in contact with either end of the ball-bearing carriage (guide) rail 140. This mechanism can be used to indicate to the user or can be interfaced with ultrasound system to restrict image acquisition when transducer compressive force is outside of constant force control. In other words, if the transducer compressive force is outside of an acceptable range, the switches 180 will be tripped and power to the probe 10 can be stopped and the user alerted as to the undesired condition. In the case when the constant force mechanism is directly incorporated into the probe 10 itself, the application of the present method involves configuring a probe transducer head 20 in a manner where relative translation is permitted with displacement of the user's hand while interfaced with a constant force spring 160 in order to maintain a constant applied force with examiner hand displacement. This method use is the same either in a configuration such as the probe handle device, which is an independent accessory, or as incorporated directly into an ultrasound transducer design.

Figure 12:
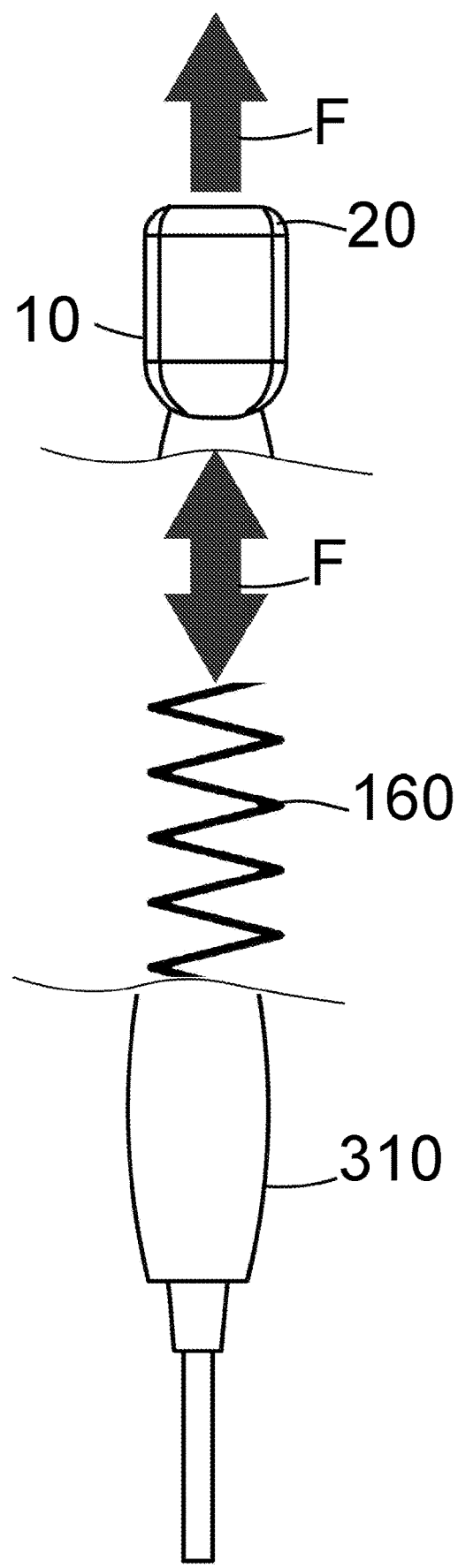
FIG. 12 is a general schematic showing the constant force principles of the present invention.

FIG. 12 generally illustrates the teachings of the present invention in which constant applied forces are indicated at 300, the user's hand displacement is indicated at 310 and the probe 10 and probe head 20 are shown. As shown, the constant force spring 160 can be compressed and store energy due to movement of the inner sleeve 130; however, the constant force spring 160 is designed to constantly apply a force to probe 10 such that as shown, the probe 10 is maintained in position against the tissue of the patient during examination. It will be appreciated that the position of the probe handle 100, 200 can vary while the applied force (F) from the probe head 20 on a patient remains constant. This results due to the sliding relative movement between the probe handle 100, 200 and the probe 10. In particular, the user grasps the handle 100, 200 (outer casing 110) and positions the probe head 40 against the tissue and the constant force spring 160 serves to apply a constant force to the patient even when the handle 100, 200 is moved relative to the patient and assumes a different position. FIGS. 3-7 shows different positions of the inner sleeve 130 and probe 10 within the outer casing 110.

The present invention provides a number of advantageous features including that the constant force mechanism, whether it be in the form of the handle accessory 100, 200 or directly incorporated into the probe, is configured to directly control the compressive forces induced by the transducer probe on the subject's body surface in performing an ultrasound exam. Additional features include but are not limited to: (1) the device eliminates user process variation by directly constraining the magnitude of transducer compressive force to a precise and constant force through utilizing constant force springs and low friction bearings which results in reduction of image artifact; (2) the device controls the magnitude of applied forces without the need for a feedback control loop, or the need for mechanical actuators that could affect image acquisition; (3) the device permits control of a wide range in magnitude of applied forces by utilizing constant force spring with various specifications interchangeably, allowing the application to dictate what target force control is required, with constant force spring specifications ranging from anywhere from sub-Newton loads to hundreds of Newton; (4) the device is economically manufacturable and adaptable to virtually any commercial probe by securing and releasing the base 30 of the probe 10 to the inner sleeve 130 of the device; (5) the device is compact over all, without any actuators or instrumentation needed to be incorporated, so the exterior handle enclosure grip can be designed to ergonomic so the examiner may perform examinations with comfort and consistency; and (6) the device can be interfaced with a contact switch 180 at each end of ball-bearing carriage rails 140 to monitor when constant force transmitted by the probe 10 is not within travel limits of constant force spring 160 control in order to indicate to user or restrict image acquisition. The present invention is designed with adaptability to fit virtually any probe dimensions, is easy to use in practice, and can significantly reduce the user-induced variability of shear-wave elastography ultrasound imaging, as well as other applications. It can be made primarily with plastic along with commercially available springs and bearing, and therefore will be economic to manufacture.

It will be appreciated that the applied force constrained depends on the spring components utilized. For example, with the use of 1.5 Newton force springs in the configuration, the applied force may be maintained within 0.1 Newton.

Moreover, the constant force ultrasound probe handle 100, 200 of the present invention further includes and can be characterized by the following points:

1. A method of acquiring ultrasound images while imposing direct constraint of the contact force between the handheld ultrasound probe and the subject by means of:
   Allow for free displacement of the ultrasound transducer or handheld probe;
   Applying a constant and fixed magnitude of force to the ultrasound transducer in the direction of the target subject with constant force springs;
   Maintaining the constant force constraint with simultaneous displacement of the ultrasound probe without the need for a feedback control loop;

2. Utilizes constant force springs with a fixed magnitude of force
   Incorporating various thickness specifications of constant force springs in order to mediate the magnitude of constant force that is constrained;
   Incorporates a number of constant force spring configurations including laminar, tandem, back-to-back or pulley mounting to mediate the magnitude of constant force constraint;
   Incorporates a varying number of constant force springs to mediate the magnitude of constant force that is constrained;
3. Utilizes constant force springs that the magnitude may be varied directly
   Incorporating springs made of shape memory alloy such as nitinol, which the magnitude of force can be mediated through temperature control to regulate material transition rate
4. Incorporates a mechanism for locking the probe displacement and disengaging the constant force constraint if desired.
5. A system that:
   Interfaces with ultrasound probes to capture an ultrasound image of a target through a skin surface;
   Permits a range of displacement of the ultrasound probe along bearing surface
   Maintains a fixed and constant force to the ultrasound probe in the direction of the target subject by means of constant force springs;
   Maintains the magnitude of constant force constraint while the ultrasound probe displaces freely along bearing surface.
6. A system that:
   Interfaces with ultrasound probes to capture an ultrasound image of a target through a skin surface;
   Permits a range of displacement of the ultrasound probe along bearing surface;
   Maintains a fixed and constant force to the ultrasound probe in the direction of the target that is adjustable by regulating the temperature environment of shape memory alloy constant force springs;
   Maintains the magnitude of constant force constraint while the ultrasound probe displaces freely along bearing surface.
7. System that is adaptable for how it is interfaced with an ultrasound probe:
   Interchangeable with range of handheld ultrasound probes, or;
   Permanently fixed to ultrasound probe
8. System that contains a mechanism to lock the ultrasound probe displacement and disengage the constant force constraint for traditional examination.
9. A system that is able to be fully sterilized for applicable applications with a risk of infection.
   Incorporates adjustment of the number of constant force springs engaged or the configuration of constant force springs in order to mediate the magnitude of constant-force constraint.
   Incorporates interchangeable springs with varying thickness specifications in order to mediate the magnitude of constant force constraint.
   Incorporates hard-limit contact switches at the limits of the handheld probe's allowable travel which can by instrumented in order to interface with the ultrasound system to:
   Restrict image acquisition to where probe is constant force controlled;
   Indicate to examiner when limit of ultrasound probe displacement is reached.

Additional features are as follows:
Device eliminates examiner process variation by directly constraining the magnitude of transducer compressive force to a precise and constant force through utilizing constant force springs and low friction bearings which results in reduction of image artifact;
it controls the magnitude of applied forces without the need for a feedback control loop, or the need for mechanical actuators that could affect image acquisition;
it permits control of a wide range in magnitude of applied forces by utilizing constant force spring with various number, thickness specifications, or arrangement to mediate the magnitude of constant force constraint, allowing the application to dictate what target force control is required;
it permits a method to easily lock the ultrasound probe position and disengage the constant force constraint for traditional examination, without having to remove the device mechanism.
Magnitude of constant force constraint mediated by permitting easy adjustment to the number and orientation, or easy interchange of constant force springs with different thickness specification within the same constant force probe handle, or by offering a range of handles with different parameters.
   Low constant force constraint for sensitive applications or superficial tissue targeted for imaging
   Higher constant force constraint for deeper target tissues.
Magnitude of constant force constraint alternatively mediated by utilizing constant force springs made of shape memory alloy materials such as nitinol. A simple mechanism for regulating (including through direct inductive heating or with electrical current) the temperature of the spring can vary the transition rate of the material which directly adjusts the magnitude of constant force constraint within the same spring.
it is economically manufacturable and adaptable to virtually any commercial probe by interchangeably securing and releasing the base (2) of the probe (1) to the interior sleeve (5) of the device;
it is compact over all, without any actuators or instrumentation needed to be incorporated, so the exterior handle enclosure grip (11) can be designed to ergonomic so the examiner may perform examinations with comfort and consistency;
it can be interfaced with a contact switch (12) at each end of ball-bearing carriage rails (8) to monitor when constant force transmitted by the probe (1) is not within travel limits of constant force spring (9) control in order to indicate to examiner or restrict image acquisition.

Advantages:
Can significantly reduce examiner-induced variability such as movement artifact in standard ultrasound imaging protocols, specific shearwave elastography imaging error, as well as other applications, ultimately improving patient diagnostics:
   Standardized imaging conditions across examiners and patients, and between repeated diagnostic protocols;
   Avoid image motion of standard ultrasound image and enhance contrast;
   Steady imaging to enhance ultrasound guided procedures and reduce complication rates;

Avoid unreliable outcomes of ultrasound shearwave elastography where contact pressure artifact expected;

Reduced imaging exam times.

System is easy to use in practice, permits examiner to perform consistent exams

Reduced demand on examiner steadiness;

Comfortable handling for sustained imaging sessions;

No additional steps necessary

System design can be adaptable, either as a standalone accessory device that is interchangeable with virtually any commercial probe, or as a fixed addition to current handheld probe designs.

It can be made primarily with plastic along with commercially available springs and bearing, and therefore will be economic to manufacture and maintain.

It can be sterilized for use in applications such as intraoperative examination or superficial ultrasound guided procedures, retaining a low risk of infection inherent to these procedures.

Due to an economic design, can be packages and manufactured and marketed a number of ways for affordability.

Method can be applied to a standalone device that is interchangeable with many probes or a fixed addition to handheld ultrasound probe, or a method that is applied directly to ultrasound probe design.

Does not require complex electromechanical system, with many expensive components, and the potential for malfunctions It is to be understood that like numerals in the drawings represent like elements through the several figures, and that not all components and/or steps described and illustrated with reference to the figures are required for all embodiments or arrangements.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present disclosure, which is set forth in the following claims.

What is claimed is:

1. A probe handle accessory for use with a probe comprising:

an outer housing having a first hollow interior and an outer surface for being gripped by a user;

an inner sleeve that is disposed within the first hollow interior and moves axially therein, the inner sleeve having a second hollow interior that is configured to receive the probe and the inner sleeve is configured for securely holding the probe in place within the second hollow interior; and at least one constant force spring that is coupled to the outer housing and to the inner sleeve and configured to apply a force to the inner sleeve in a distal direction for maintaining the probe in position against a surface of interest during examination thereof, while permitting axial movement of the inner sleeve within the outer housing;

wherein the constant force spring comprises a rolled ribbon spring and is wound about a support; and wherein the support comprises a pulley that is coupled to a lower housing extension of the inner sleeve and moves axially together with the inner sleeve within and relative to the outer housing, one end of the constant force spring being would about the pulley.

2. The probe handle accessory of claim 1, wherein the outer housing includes an enlarged portion at an open distal end for accommodating an enlarged transducer head of the probe and an opposite proximal end of the outer housing includes an opening for allowing passage of a cord associated with the probe.

3. The probe handle accessory of claim 1, further including at least one guide along which the inner sleeve travels in an axial direction, the at least one guide being configured to define a degree of axial travel permitted by the inner sleeve within the outer housing.

4. The probe handle accessory of claim 3, wherein the inner sleeve includes a coupling member that mates with the at least one guide for constraining lateral movement of the inner sleeve while permitting axial movement.

5. The probe handle accessory of claim 4, wherein the at least one guide comprises a pair of guides in the form of two guide rails disposed along inner surfaces of two opposing side walls of the outer housing and the coupling member comprises two coupling members disposed along outer surfaces of opposing sides of the inner sleeve, each guide rail having a pair of longitudinal grooves that receive complementary protrusions formed along each coupling member for securely coupling the inner sleeve to the outer housing while permitting axial movement of the inner sleeve.

6. The probe handle accessory of claim 4, wherein the at least one guide comprises two guide rails disposed along a rear wall of the outer housing and the coupling member comprises a single coupling member disposed along a rear wall of the inner sleeve, the two guide rails having a pair of longitudinal grooves that receive complementary protrusions formed long the coupling member for securely coupling the inner sleeve to the outer housing while permitting axial movement of the inner sleeve.

7. The probe handle accessory of claim 1, wherein the at least one constant force spring is configured to apply an at least substantially fixed magnitude of force to the inner sleeve in the distal direction over a range of axial positions of the inner sleeve within the outer housing.

8. The probe handle accessory of claim 1, wherein the force being applied to the inner sleeve comprises an at least substantially constant force over a range of axial positions of the inner sleeve within the outer housing.

9. The probe handle accessory of claim 1, further including at least two sensors for detecting a position of the inner sleeve within the outer housing.

10. The probe handle accessory of claim 9, wherein one sensor is disposed at a maximum extended position of the inner sleeve and another sensor is disposed at a maximum retracted position of the inner sleeve.

11. The probe handle accessory of claim 10, wherein the one sensor comprises a first switch that is closed by contact with the inner sleeve when the inner sleeve assumes the maximum extended position and the other sensor comprises a second switch that is closed by contact with the inner sleeve when the inner sleeve assumes the maximum retracted position.

12. The probe handle accessory of claim 1, wherein the at least one constant force spring is configured to move between a wound retracted position and an unwound extended position.

13. The probe handle accessory of claim 1, wherein the inner sleeve is at least partially open at two ends and has an open side, with the second hollow interior being configured to laterally receive the probe through the open side.

14. The probe handle accessory of claim 1, wherein a rolled section of the rolled ribbon spring is located directly below a floor of the inner sleeve which is configured to position the probe above the rolled section.

15. The probe handle accessory of claim 1, wherein one end section of the rolled ribbon spring extends longitudinally along a rear face of the inner sleeve between the inner sleeve and the outer housing.

16. The probe handle accessory of claim 1, wherein an axis of the support about which the rolled ribbon spring is wound is perpendicular to a rear wall of the outer housing.

17. The probe handle accessory of claim 1, wherein an axis of the support about which the rolled ribbon spring is wound is perpendicular to two opposing side walls of the outer housing.

18. A probe system that is configured for placement against and movement along a body of interest comprising:
 a probe having a head portion that is intended for placement against the body of interest;
 a probe handle accessory for holding the probe, the probe handle accessory comprising:
  an outer housing having a first hollow interior and an outer surface for being gripped by a user;
  an inner sleeve that is disposed within the first hollow interior and moves axially therein, the inner sleeve having a main housing that defines a second hollow interior that receives the probe with the probe being fixedly held in place within the second hollow interior, the inner sleeve having a lower housing extension that is integral to the main housing with a floor of the inner sleeve separating the second hollow interior and the lower housing extension; and
  at least one constant force spring that is coupled to the outer housing and to a support that is coupled to the lower housing extension of the inner sleeve and configured to apply a force to the inner sleeve and to the probe in a distal direction for maintaining the probe in position against the body of interest during examination thereof, while permitting axial movement of the inner sleeve and probe within the outer housing due to counter forces being applied to the probe;
  wherein the constant force spring comprises a rolled ribbon spring that is wound about the support which moves axially with the inner sleeve and
  wherein the support comprises a pulley that is coupled to the lower housing extension of the inner sleeve and moves axially together with the inner sleeve within and relative to the outer housing, one end of the constant force spring being wound about the pulley.

19. The probe system of claim 18, wherein the probe comprises an ultrasound probe and the body of interest is tissue.

20. The probe system of claim 18, further including at least one guide along which the inner sleeve travels in an axial direction, the at least one guide being configured to define a degree of axial travel permitted by the inner sleeve within the outer housing and wherein the inner sleeve includes a coupling member that mates with the at least one guide for constraining lateral movement of the inner sleeve while permitting axial movement, wherein the at least one guide is fixedly attached to the outer housing and the coupling member moves axially and is constrained along one edge of the at least one guide.

21. The probe system of claim 20, wherein the at least one constant force spring comprises a pair of rolled metal strips each of which is configured to apply an at least substantially fixed magnitude of force to the inner sleeve in the distal direction over a range of axial positions of the inner sleeve within the outer housing, wherein the at least one guide is disposed between the pair of rolled metal strips.

22. The probe system of claim 21, wherein the pulley comprises a pair of pulleys that are fixed to the lower housing extension, while the pair of rolled metal strips are fixedly attached to the outer housing and are wound about coils associated with the pair of pulleys.

23. The probe system of claim 18, wherein the at least one constant force spring is configured to maintain an at least substantially constant force to the probe while the probe is axially displaced due to longitudinal movement of the inner sleeve within the outer housing.

24. The probe system of claim 18, wherein the at least one constant force spring is made from a shape memory alloy.

25. The probe system of claim 18, further including at least two sensors for detecting a position of the inner sleeve within the outer housing.

26. The probe system of claim 25, wherein one sensor is disposed at a maximum extended position of the inner sleeve and another sensor is disposed at a maximum retracted position of the inner sleeve.

27. The probe system of claim 26, wherein the one sensor comprises a first switch that is closed by contact with the inner sleeve when the inner sleeve assumes the maximum extended position and the other sensor comprises a second switch that is closed by contact with the inner sleeve when the inner sleeve assumes the maximum retracted position.

28. The probe system of claim 27, wherein the first switch and the second switch are in communication with a controller that is configured to perform at least one operation selected from the group consisting of: (1) restricting image acquisition if one of the first switch and the second switch is closed, and (2) alerting a user when one of the first switch and the second switch is closed which is indicative of probe displacement reaching a maximum limit.

* * * * *